United States Patent [19]

Wovcha

[11] 4,035,236
[45] July 12, 1977

[54] PROCESS FOR PREPARING 9α-HYDROXYANDROSTENEDIONE

[75] Inventor: Merle G. Wovcha, Kalamazoo, Mich.

[73] Assignee: The Upjohn Company, Kalamazoo, Mich.

[21] Appl. No.: 625,653

[22] Filed: Oct. 24, 1975

[51] Int. Cl.$^2$ .................................. C07B 29/02
[52] U.S. Cl. ........................... 195/51 G; 195/112
[58] Field of Search ................................ 195/51 G

[56] References Cited

U.S. PATENT DOCUMENTS 3,759,791  9/1973  Marsheck et al. ............... 195/51 G

OTHER PUBLICATIONS

Agr. Biol. Chem., vol. 33, No. 11, pp. 1644–1650, 1969.

Biochimica et Biophysica Acta, vol. 62, pp. 541–547, (1962).

*Primary Examiner*—Alvin E. Tanenholtz
*Attorney, Agent, or Firm*—Roman Saliwanchik

[57] ABSTRACT

Mutants which are used in a novel microbiological process to selectively degrade steroids having 17-alkyl side chains of from 2 to 10 carbon atoms, inclusive, to 9α-hydroxyandrostenedione (9α-OH AD). 9α-OH AD is a valuable intermediate to make useful steroids.

11 Claims, No Drawings

PROCESS FOR PREPARING 9α-HYDROXYANDROSTENEDIONE

BACKGROUND OF THE INVENTION

The transformation of steroids by microorganisms has been widely studied and documented. Apparently, the earliest such work was by Mamoli and Vercellone in 1937, Ber. 70, 470 and Ber. 70, 2079. They disclosed the reduction of 17-ketosterioids to 17β-hydroxysteroids by fermenting yeast. More recently, Peterson and Murray disclosed the 11α-hydroxylation of progesterone with the fungus *Rhiopus nigricans*; see, U.S. Pat. No. 2,602,769 (1952). Also recently, Kraychy et al. in U.S. Pat. No. 3,684,657 (1972) discloses the selective microbiological degradation of steroidal 17-alkyls by fermenting a steroid containing at least 8 carbons in the 17-alkyl side chain with Mycobacterium sp. NRRL B-3683 to prepare androst-4-ene-3,17-dione, androst-1,4-diene-3,17-dione, and 20α-hydroxymethyl -pregna-1,4-dien-3-one. Even more recently, Marsheck et al. in U.S. Pat. No. 3,759,791 (1973) disclose the selective microbiological preparation of androst-4-ene-3,17-dione by fermenting a steroid of the cholestane or stigmastane series containing at least 8 carbons in the 17-alkyl side chain with Mycobacterium sp. NRRL B-3805.

BRIEF SUMMARY OF THE INVENTION

Mutants which are characterized by their ability to selectively degrade steroids having 17-alkyl side chains of from 2 to 10 carbon atoms, inclusive, and accumulate 9α-hydroxyandrostenedione, hereinafter referred to as 9α-OH AD, in the fermentation beer. These mutants can be obtained from microorganisms of the following genera by using the mutation procedures disclosed herein or other mutation procedures: Arthrobacter, Bacillus, Brevibacterium, Corynebacterium, Microbacterium, Mycobacterium, Nocardia, Protaminobacter, Serratia, and Streptomyces. A preferred genera is Mycobacterium. Exemplary species of this genera are *M. phlei*, *M. smegmatis*, *M. rhodochrous*, *M. mucosum*, *M. fortuitum*, and *M. butyricum*. Specifically exemplified herein is a novel mutant microorganism, *Mycobacterium fortuitum*, NRRL B-8119, which is used to selectively degrade steroids having 17-alkyl chains of from 2 to 10 carbon atoms, inclusive, to 9α-hydroxyandrostenedione, hereinafter referred to as 9α-OH AD. Examples of suitable steroid substrates are sitosterols, cholesterol, stigmasterol, campesterol, and like steroids with 17-alkyl side chains of from 2 to 10 carbon atoms, inclusive. These steroid substrates can be in either the pure or crude form.

DETAILED DESCRIPTION OF THE INVENTION

The Microorganisms

Mutants which are characterized by their ability to selectively degrade steroids having 17-alkyl side chains of from 2 to 10 carbon atoms, inclusive, and accumulate 9α-OH AD in the fermentation beer can be obtained by mutating microorganisms of the following genera: Arthrobacter, Bacillus, Brevibacterium, Corynebacterium, Microbacterium, Mycobacterium, Nocardia, Protaminobacter, Serratia, and Streptomyces. *Mycobacterium fotuitum*, ATCC 6842, has been mutated, as disclosed herein, to give a novel laboratory mutant microorganism. The 1974 ATCC Catalogue discloses the following alongside the listing of ATCC 6842: "J.C. Cruz 2. Cold abscess. Acta Med. Rio de Janeiro 1:1 (1936). Medium 90 37C." *M. fortuitum*, ATCC 6842, degrades sterols non-selectively to small molecular weight compounds, e.g. $CO_2 + H_2O$. Thus, this microorganism is not suitable as a selective steroid degrader.

Mutation of *M. fortuitum*, ATCC 6842, using nitrosoquanidine has resulted in the production of a novel mutant which selectively degrades steroids having 17-alkyl side chains of from 2 to 10 carbon atoms, inclusive, to produce 9α-OH AD. This mutant microorganism of *M. fortuitum* has been given the accession number NRRL B-88119, by the Northern Regional Research Laboratory, U.S. Department of Agriculture, Peoria, Ill. U.S.A., where it has been deposited in the permanent collection. A subculture of this microorganism is freely available from this depository by request made thereto. It should be understood that the availability of the culture does not constitute a license to practice the subject invention in derogation of patent rights granted with the subject instrument by governmental action.

The morphology and drug sensitivities of *M. fortuitum*, NRRL B-8119, are indistinguishable from that of the parent *M. fortuitum*, ATTC 6842. Both *M. fortuitum* cultures are acid-fast non-motile, non-spore bacilli belonging to the family Mycobacteriaceae of the order Actinomycetales. According to Runyons classification, Runyon E. H. 1959 Med. Clin. North America 43:273, it is a nonchromogenic group IV mycobacterium, i.e., it grows rapidly at low temperature to produce nonpigmented colonies on relatively simple media.

*M. fortuitum* ATCC 6842 and *M. fortuitum* NRRL B-8119, are clearly distinguishable in their action on steroid molecules. As disclosed above, *M. fortuitum* ATCC 6842 is a non-selective degrader of steroids, whereas *M. fortuitum* NRRL B-8119 is a selective degrader. This property of *M. fortuitum* NRRL B-8119 makes it highly useful, as disclosed herein.

The mutation of *M. fortuitum* ATCC 6842 to give *M. fortuitum* NRRL B-8119 was accomplished by the use of nitrosoguanidine. The details of the procedure are described infra. Though mutation procedures are generally known in the art, there is not known art which teaches or even suggests the type of mutants, if any, which might be obtained by use of the subject mutation procedure. Also, though the mutation and transformation procedures, disclosed herein, are detailed for a Mycobacterium, it should be understood that similar or equivalent procedures can be used with microorganisms of the other genera, as disclosed herein.

The Transformation Process

The selective transformation of the subject invention can be effected in a growing culture of *M. fortuitum* NRRL B-8119 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen surces include cornsteep liquor, yeast, autolyzed brewer's yeast with milk solids, soybean meal, cottonseed meal, cornmeal, milk solids, pancreatic digest of casein, fish meal, distillers'solids, animal peptone liquors, meat and bone scraps, ammonium salts and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

The transformation process can range from about 72 hours to 15 days. The incubation temperature during the transformation process can range from about 25° to about 37° C., with 30° C. being preferred. The contents of the transformation vessel are aerated with sterilized air and agitated to facilitate growth of the microorganism, and, thus, enhance the effectiveness of the transformation process.

Upon completion of the transformation process, as evidenced by thin layer chromatography using silica gel plates (E. Merck, Darmstadt) and a solvent system consisting of 2:3 (by volume) ethyl acetate-cyclohexane, the desired transformed steroid is recovered by means well known in the art. For example, the fermentation (transformation) reaction mixture, including the fermentation liquor and cells, can be extracted with a water-immiscible organic solvent for steroids. Suitable solvents are methylene chloride (preferred), chloroform, carbon tetrachloride, ethylene chloride, trichloroethylene, ether, amyl acetate, benzene and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

The extracts can be filtered through diatomaceous earth and the filtrate vacuum distilled to dryness. The resulting residue containing the desired transformed sterioid then can be dissolved in 10% chloroform in methanol and this then concentrated with nitrogen on a steam bath until crystals appear. The solution then can be cooled to room temperature and filtered to remove precipitated steroid. The desired transformed steroid can also be obtained from the remaining supernatuant upon evaporation of the solvent in the supernatant.

The desired product of the subject invention transformation process is the known steroid intermediate 9α-OH AD. The 9α-hydroxy compounds of the androstane series are useful as antiandrogenic, antiestrogenic and antifertility agents. These 9α-hydroxy steroids are also useful in the preparation of other therapeutically useful steroids. For example, the 9α-hydroxy-11-unsubstituted steroids can be easily dehydrated to the valuable 9(11)-dehydro steriods in accordance with methods known in the art, e.g., with thionyl chloride in the presence of pyridine. The 9(11)-dehydro compounds thus obtained are known intermediates in the production of highly active compounds. For example, the 9(11)-dehydro steroids can be easily converted to the corresponding 9α-halo-11β-hydroxy compounds in accordance with procedures known in the art, e.g., U.S. Pat. No. 2,852,511 for the preparation of 9α-halohydrocortisone.

The following examples are illustrative of the process and products of the subject invention but are not to be construed as limiting. All percentages are by weight and all solvent mixture proportions are by volume unless otherwise noted.

EXAMPLE 1

Preparation of Mutant *M. fortuitum* NRRL B-8119

From *M. fortuitum* ATCC 6842 a. Nitrosoguanidine Mutagenes is

Cells of *M. fortuitum* ATCC 6842 are grown at 28° C. in the following sterile seed medium:

| | |
|---|---|
| Nutrient Broth (Difco) | 8 g/liter |
| Yeast Extract | 1 g/liter |
| Sodium Propionate | 0.5 g/liter |
| Distilled Water, q.s. | 1 liter |

The pH is adjusted to 7.0 with 1N NaOH prior to sterilization at 121° C. for 20 minutes.

The cells are grown to a density of about $5 \times 10^8$ per ml, pelleted by centrifugation, and then washed with an equal volume of sterile 0.1 M sodium citrate, pH 5.6. Washed cells are resuspended in the same volume of citrate buffer, a sample removed for titering (cell count), and nitrosoguanidine added to a final concentration of 50 μg/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile minimal salts medium, minus a carbon source, consisting of the following:

| | |
|---|---|
| $NH_4NO_3$ | 1.0 g/liter |
| $K_2HPO_4$ | 0.25 g/liter |
| $MgSO_4 \cdot 7H_2O$ | 0.25 g/liter |
| NaCl | 0.005 g/liter |
| $FeSO_4 \cdot 7H_2O$ | 0.001 g/liter |
| Distilled Water, q.s. | 1 liter |

The pH is adjusted to 7.0 with 1N HCl prior to sterilization at 121° C. for 20 minutes. The cells are then plated out to select for mutants.

b. Selection And Isolation Of Mutant M. fortuitum NRRL B-8119.

Mutagenized cells, as described above, are diluted and spread onto plates containing a medium consisting of the following (modified from Fraser and Jerrel. 1963. J. Biol. Chem. 205:291-295):

| | |
|---|---|
| Glycerol | 10.0 g/liter |
| $Na_2HPO_4$ | 8.4 g/liter |
| $KH_2PO_4$ | 4.5 g/liter |
| $NH_4Cl$ | 2.0 g/liter |
| $MgSO_4 \cdot 7H_2O$ | 0.3 g/liter |
| $FeCl_3 \cdot 6H_2O$ | 0.05 g/liter |
| Distilled Water, q.s. | 1 liter |

Agar (15 g/liter) is added, and the medium is autoclaved at 121° C. for 30 minutes and then poured into sterile Petri plates.

Growth on this medium eliminates most nutritional auxotrophes produced by the mutagensis procedure, e.g. cultures that require vitamins, growth factors, etc, in order to grow on chemically defined medium are eliminated. After incubation at 28° C. for about 7 days, the resulting colonies are replicated to test plates suitable for selecting mutants and then back onto control plates containing the glycerol-based medium. The test plates are prepared as described by Peterson, G. E., H. L. Lewis and J. R. Davis. 1962. "Preparation of uniform dispersion of cholesterol and other water-insoluble carbon sources in agar Media." J. Lipid Research 3:275-276. The minimal salts medium in these plates is as described above in section (a) of Example 1. Agar (15 g/liter), and an appropriate carbon source (1.0 g/liter), such as sitosterol or androstenedione (AD), are added and the resulting suspension autoclaved for 30 minutes at 121° C . The sterile, hot mixture is then poured into a sterile blender vessel, blended for several minutes, and then poured into sterile Petri plates. Foaming tends to be a problem in this procedure but can be reduced by blending when the mixture is hot and by flaming the surface of the molten agar plates. In this manner uniform dispersions of water-insoluble carbon sources are obtained which facilitates the preparation of very homogenous but opaque agar plates.

Colonies which grew on the control plates, but not on test plates containing AD as the sole carbon source, are purified by streaking onto nutrient agar plates. After growth at 28° C., individual clones are picked from the nutrient agar plates with sterile toothpicks and retested by inoculating grided plates containing AD as the carbon source. Purified isolates which still exhibit a phenotype different from the parental cultures are then evaluated in shake flasks.

c. Shake Flask Evaluation

Shake flasks (500 ml) contain 100 ml of biotransformation medium consisting of the following ingredients:

| Glycerol | 10.0 g/liter |
|---|---|
| $Na_2HPO_4$ | 8.4 g/liter |
| $KH_2PO_4$ | 4.5 g/liter |
| $NH_4Cl$ | 2.0 g/liter |
| $MgSO_4.7H_2O$ | 0.3 g/liter |
| $FeCl_3.6H_2O$ | 0.05 g/liter |
| Distilled Water, q.s. | 1 liter |

Soyflour (1 g/liter) is blended into the medium and then sitosterol (10 g/liter) is also blended into the medium, After the flasks are autoclaved for 20 minutes at 121° C., they are cooled to 28° C. and then inoculated with 10 ml of seed growth prepared as follows:

The purified isolates from part (b) are grown on agar slants at 28° C. A loop of cells taken from a slant is used to inoculate a 500-ml flask containing 100 ml of sterile seed medium consisting of the following ingredients:

| Nutrient Broth (Difco) | 8 g/liter |
|---|---|
| Yeast Extract | 1 g/liter |
| Glycerol | 5 g/liter |
| Distilled Water, q.s. | 1 liter |

The pH is adjusted to 7.0 with 1N Na OH prior to autoclaving the flasks at 121° C. for 20 minutes. The seed flasks are incubated at 28° C. for 72 hours.

As disclosed above, 10 ml of seed growth is then used to inoculate each 500-ml flask containing 100 ml of sterile transformation medium. The flasks are then incubated at 28° to 30° C. on a rotary shaker and sampled at various intervals. Ten ml samples are removed and extracted by shaking with 3 volumes of methylene chloride. Portions of the extracts are analyzed by thin layer chromatography using silica gel and the solvent system described above, i.e., 2:3 (by volume) ethyl acetatecyclohexane, and by gas-liquid chromatography. Evidence of the presence of 9α-OH AD confirms the selective degradation of sitosteriol by the novel mutant produced from the parent *M. fortuitum* ATCC 6842.

EXAMPLE 2

Transformation of Sitosterol To 9α-OH AD

The medium used is the same as in Example 1c. This medium is sterilized by heating 30 minutes at 121° C., whereupon it is cooled to 30° C. and then inoculated with 10 parts of a seed culture of the mutant mycobacterium *M. fortuitum* NRRL B-8119, prepared as described in Example 1 (c). The inoculated mixture is incubated at 30° C. for 336 hours with agitation to promote submerged growth. Following incubation, the mixture is extracted with methylene chloride. The extract is filtered through diatomaceous earth and the filtrate is vacuum distilled to dryness. The residue is taken up in 10% chloroform in methanol and then concentrated with nitrogen on a steam bath until crystals appear. The solution is then cooled to room temperature and filtered to remove the precipitated sitosterols. From the supernatant, on evaporation of solvent, a good yield of crude 9α-hydroxy-4-androstene-3,17-dione is obtained. A trace of 9α-hydroxy-4-androstene-3-one-17ol is shown by thin layer chromatography to be present.

EXAMPLE 3

By substituting cholesterol for sitosterol in Example 2 there is obtained 9α-OH AD.

EXAMPLE 4 By substituting stigmasterol in Example 2 for sitosterol there is obtained 9α-OH AD.

EXAMPLE 5

By substituting campesterol for sitosterol in Example 2 there is obtained 9α-OH AD.

EXAMPLE 6

By adding a combination of any of the steroids in Example 25, in addition to sitosterol, or in place of sitosterol, in Example 2 there is obtained 9α-OH AD.

EXAMPLE 7

The crude 9α-OH AD obtained in Examples 2–6 is purified by the following procedure. The insolubles are removed from fermentation broth prepared as described in Examples 2–6 by filtration or centrifugation. The separated cake is washed with a suitable amount of water and the wash liquid combined with the solids-free filtrate. The cake fraction is leached with an aqueous acetone solution (1:4), the acetone removed and the resulting aqueous stream combined with the solids-free filtrate and wash. Residual sterols may be recovered from the leached cake fraction by extracting with methylene chloride, removal of the solvent and subsequent crystallization.

The filtered beer fraction is extracted twice with one half volume of butyl acetate at a pH of 4.0 and the spent beer discarded. Pooled extracts of the beer are washed with one fourth volume of 5% sodium bicarbonate to remove acidic components that may be produced in the fermentation.

The pooled neutralized extracts are concentrated to about 2% of the beer volume, cooled and the purified product 9α-OH AD crystallized. The product is obtained by the usual methods of filtration and drying. This product assays greater than 95% purity by liquid chromatography assay. Additional 9α-OH AD may be obtained from the mother liquors by further concentration and the addition of cyclohexane to reduce the solubility.

EXAMPLE 8

By substituting a microorganism from the genera Arthrobacter, Bacillus, Brevibacterium, Corynebacterium, Microbacterium, Nocardia, Protaminobacter, Serratia, and Streptomyces, in Example 1 for *Mycobacterium fortuitum* ATCC 6842 there are obtained mutant microorganisms which are characterized by their ability to selectively degrade steroids having 17-alkyl side chains of from 2 to 10 carbon atoms, inclusive, and accumulate 9α-OH AD in the fermentation beer.

EXAMPLE 9

By substituting the mutants obtained in Example 8 for *M. fortuitum* NRRL B-8119 in Examples 2-7, there is obtained 9α-OH AD.

EXAMPLE 10

By substituting a microorganism selected from the group consisting of *Mycobacterium phlei, M. smegmatis, M. rhodochrous, M. mucosum,* and *M. butyricum* for *M. fortuitum* ATCC 6842 in Example 1 there are obtained mutant microorganisms which are characterized by their ability to selectively degrade steroids having 17-alkyl side chains of from 2 to 10 carbon atoms, inclusive, and accumulate 9α-OH AD in the fermentation beer.

EXAMPLE 11

By substituting the mutants obtained in Example 10 for *M. fortuitum* NRRL B-8119 in Examples 2-7, there is obtained 9α-OH AD.

I claim :

1. A process for preparing 9α-hydroxyandrostenedione whih comprises culvating *Mycobacterium fortuitum* NRRL B-8119 in an aqueous nutrient medium under aerobic conditions in the presence of a steroid containing from 2 to 10 carbon atoms, inclusive, in the 17-alkyl side chain.

2. A process according to claim 1, wherein said steroid is sitosterol.

3. A process, according to claim 1, wherein said steroid is cholesterol.

4. A process, according to claim 1, wherein said steroid is stigmasterol.

5. A process, according to claim 1, wherein said steroid is campesterol.

6. A process for preparing 9α-hydroxyandrostenedione which comprises cultivating *Mycobacterium fortuitum* NRRL B-8119 in an aqueous nutrient medium under aerobic conditions in the presence of a mixture of two or more steroids wherein each steroid contains from 2 to 10 carbon atoms, inclusive, in the 17alkyl side chain.

7. A process accordng to claim 6, wherein said steroid mixture is selected from the group consisting of sitosterol, cholesterol, stigmasterol, and campesterol.

8. A process for preparing 9α-hydroxyandrostenedione which comprises cultivating a mutant microorganism selected from the group consisting of Arthrobacter, Bacillus, Brevibacterium, Corynebacterium, Microbacterium, Protaminobacter, Serratia, and Streptomyces, said mutant being characterized by its ability to selectively degrade steroids having 17-alkyl side chains of from 2 to 10 carbon atoms, inclusive, and accumulate 9α-hydroxyandrostenedione in the fermentation beer, in an aqueous nutrient medium under aerobic conditions in the presence of a steroid containing from 2 to 10 carbon atoms, inclusive, in the 17-alkyl side chain.

9. A process, according to claim 8, wherein said mutant microorganism is cultivated in an aqueous nutrient medium under aerobic conditions in the presence of a mixture of two or more steroids wherein each steroid contains from 2 to 10 carbon atoms, inclusive, in the 17-alkyl side chain.

10. A process, according to claim 8, wherein said steroid is selected from the group consisting of sitosterol, cholesterol, stigmasterol, and campesterol.

11. A process, according to claim 9, wherein said steroid mixture is selected from the group consisting of sitosterol, cholesterol, stigmasterol, and campesterol.

* * * * *

UNITED STATES PATENT OFFICE
CERTIFICATE OF CORRECTION

Patent No. 4,035,236              Dated   July 12, 1977

Inventor(s)   Merle G. Wovcha

It is certified that error appears in the above-identified patent and that said Letters Patent are hereby corrected as shown below:

Column 1, line 10, for "17-ketosterioids" read -- 17-ketosteroids --; line 13, for "Rhiopus" read -- Rhizopus --. Column 2, lines 7-8, for "nitrosoquanidine" read -- nitrosoguanidine --; line 13, for "B-88119" read -- B-8119 --; line 26, for "non-spore" read -- non-spore-forming --; line 45, for "not" read -- no --. Column 3, line 46, for "sterioid" read -- steroid --; line 61, for "sterioids" read -- steroids --. Column 5, line 8, for "dispersion" read -- dispersions --; line 47, for "medium," read -- medium. --; line 60, for "Na OH" read -- NaOH --. Column 6, line 6, for "sitosteriol" read -- sitosterol --; line 47, for "Example 25" read -- Examples 2-5 --. Column 7, line 46, claim 1, for "whih" read -- which -- and for "culvating" read -- cultivating --. Column 8, line 4, claim 2, for "process" read -- process, --; line 17, claim 6, for "17alkyl" read -- 17-alkyl --; line 19, claim 7, for "process" read -- process, -- and for "accordng" read -- according --.

*Signed and Sealed this*

*Eighth* Day of *November 1977*

[SEAL]

Attest:

RUTH C. MASON
*Attesting Officer*

LUTRELLE F. PARKER
*Acting Commissioner of Patents and Trademarks*